(12) United States Patent
Walker

(10) Patent No.: US 7,270,740 B2
(45) Date of Patent: Sep. 18, 2007

(54) STARTUP OF AN OLEFINS PRODUCTION PLANT

(75) Inventor: James H. Walker, Crosby, TX (US)

(73) Assignee: Equistar Chemicals, LP, Houston, TX (US)

( * ) Notice: Subject to any disclaimer, the term of this patent is extended or adjusted under 35 U.S.C. 154(b) by 426 days.

(21) Appl. No.: 11/087,848

(22) Filed: Mar. 23, 2005

(65) Prior Publication Data

US 2006/0217583 A1  Sep. 28, 2006

(51) Int. Cl.
*C10G 35/22* (2006.01)
*C10G 9/00* (2006.01)

(52) U.S. Cl. .............. 208/154; 208/113; 208/125; 208/130; 208/132; 585/648; 585/652; 585/951

(58) Field of Classification Search ............ None
See application file for complete search history.

(56) References Cited

U.S. PATENT DOCUMENTS 5,777,188 A * 7/1998 Reed et al. ............... 585/648
2005/0038306 A1 * 2/2005 Beech et al. .............. 585/446

* cited by examiner

*Primary Examiner*—Tam M. Nguyen
(74) *Attorney, Agent, or Firm*—Roderick W. MacDonald

(57) ABSTRACT

A method for starting up an olefin production plant without venting gases to the atmosphere wherein an artificial feed is employed in the compression zone of the plant while the furnace and quench zones remain idle, and gases from the compression and refrigeration zones of the plant are recycled to the inlet of the compression zone during startup, after which the furnace and quench zones are started up using natural feed.

5 Claims, 2 Drawing Sheets

FIG. 1 Prior Art Startup

STARTUP OF AN OLEFINS PRODUCTION PLANT

BACKGROUND OF THE INVENTION

This invention relates to starting up an olefins production plant. More particularly, this invention relates to the start up of an olefins production plant without flaring or other venting of vaporous or gaseous materials to the atmosphere during such startup.

DESCRIPTION OF THE PRIOR ART

Thermal cracking of hydrocarbons is a petrochemical process that is widely used to produce olefins such as ethylene, propylene, butenes, butadiene, and aromatics such as benzene, toluene, and xylenes. In such a plant, a hydrocarbonaceous feedstock such as ethane, naphtha, gas oil, or other fractions of whole crude oil is mixed with steam which serves as a diluent to keep the hydrocarbon molecules separated. This mixture, after preheating, is subjected to severe hydrocarbon thermal cracking at elevated temperatures (1,450° F. to 1,550° F.) in a pyrolysis furnace (steam cracker or cracker).

The cracked product from the cracker contains hot, gaseous hydrocarbons of great variety (from 1 to 35 carbon atoms per molecule, i.e., C1-C35, inclusive). This furnace product is then subjected to further processing to produce, as products of the olefin plant, various, separate and individual product streams of high purity, e.g., molecular hydrogen, ethylene, and propylene. After the separation of these individual streams, the remaining cracked product contains essentially hydrocarbons with four carbon atoms per molecule (C4's) and heavier. This remainder is fed to a debutanizer wherein a crude C4 stream is separated as overhead while a C5 and heavier stream is removed as a bottoms product.

The hot, cracked furnace product, upon leaving the furnace, is, for example, introduced into a tube-type heat exchanger wherein boiler feed water is indirectly heat exchanged with the hot product stream to quench the product to a more manageable level, and to generate high pressure steam for use elsewhere. The quench step forms a liquid pyrolysis gasoline stream which is removed from the process. After quenching, the cracked product is subjected to one or more compression steps which help liquefy essentially C5 and heavier hydrocarbons. The compressed, cracked product is, after caustic scrubbing and drying, subjected to refrigeration in what is termed a "cold box" which is really a complicated cryogenic separation zone that employs multiple pass heat exchangers to liquefy essentially all of the remaining hydrocarbons except methane, thereby leaving gaseous methane and molecular hydrogen. High purity hydrogen is separated from the cold box, and the liquefied cracked product is then subjected to multiple separation (fractionation) steps to separate from the process individual products such as methane, ethane and ethylene, propylene, C4's, C'5's, aromatics, and the like. The system of equipment and processing steps (zones) aforesaid, from the pyrolysis furnace through the demethanation step, i.e., up to the remaining fractionation steps, is the area of the olefin plant with which this invention is concerned.

For various reasons, well known in the art, such as shut down for equipment maintenance purposes, the portion of an olefin plant with which this invention is concerned is terminated temporarily as to its normal operation. Such shut down allows various pieces of equipment, and fluids therein, to cool down or warm up, depending on the equipment, to ambient conditions of temperature and pressure, and allows fluid in that equipment to stop flowing. Shut down also allows gaseous materials to be present in various pieces of equipment where in normal operation essentially only liquid would be present. Thus, after shut down an olefin production plant is far from its normal operating conditions as to temperature, pressure, fluid content, fluid flow, and on and on.

Once such a plant is ready to be started up so that it can regain its normal operating conditions, actually reaching such normal operating conditions can take an extended amount of time. This is so because such a plant is quite large physically, is complicated both mechanically and chemically, and involves temperatures ranging from extremely hot in the furnace to extremely cold in the cold box. During such start up time, numerous fluids, particularly non-condensed gaseous materials, are removed from certain equipment and/or generated by the start up process that are not desired as products of the process, should not be passed on to the fractionation zones aforesaid, and need to be handled in some temporary fashion until the plant is back to its normal operating conditions.

Heretofore, in the start up of such a plant, the furnace, quench, and compression zones have been started up using natural feed that is normally fed to the furnace, and this is maintained until such zones reached their normal operating conditions. This left the cold box and demethanation zones operating during start up at warmer than normal conditions, which led to the formation of large amounts of non-condensed gases that were handled by flaring (burning) to the atmosphere until the cold box and demethanation zone cooled down to their normal operating conditions. Once the cold box and the demethanation zone reached their normal operating conditions, flaring was terminated.

It is desirable to have an olefin plant start up procedure which does not require flaring to the atmosphere for obvious conservation and environmental reasons, and this invention provides such a procedure.

SUMMARY OF THE INVENTION

In accordance with this invention, there is provided a method for starting up an olefin production plant which involves maintaining the furnace and quench zones in a non-operational shut down mode while maintaining the fractionation zones downstream of the demethanation zone in their operating modes, and starting up the compression zone using an artificial feed material. After certain criteria are met, the cold box is started up, followed by the demethanation zone. During all this start up, essentially all gas formed or otherwise found in the start up equipment is recycled to the compression zone. Once the compression, refrigeration (cold box), and demethanation zones are started up using artificial feed, the furnace and quench zones are started up using natural feed, and when they are up to normal operating conditions, the use of artificial feed is terminated, whereby the plant has been started up essentially without flaring or other venting of gases to the atmosphere.

DETAILED DESCRIPTION OF THE INVENTION

Figure 1:
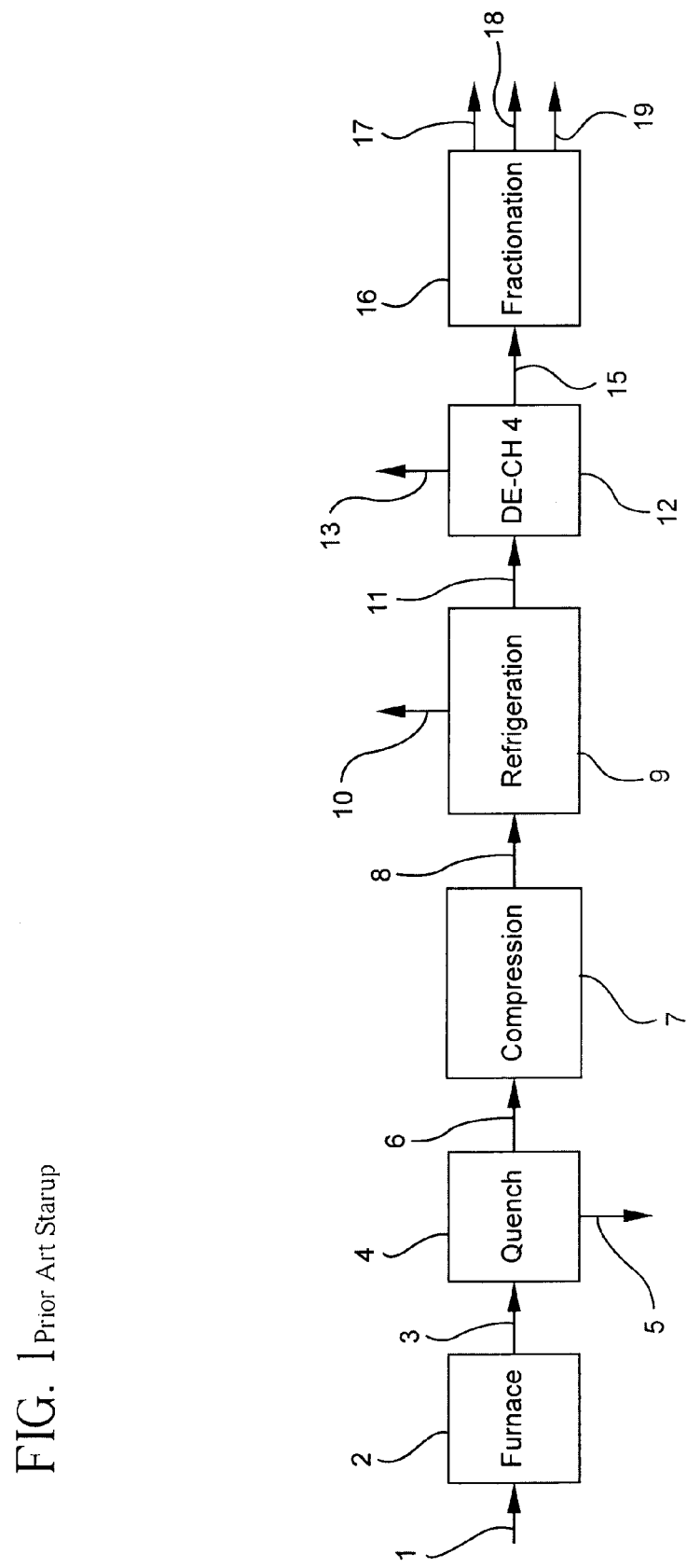
FIG. 1 shows a block flow diagram of a typical olefin production plant from the pyrolysis furnace through the product fractionation zones, as described above, when being started up in accordance with the prior art.

FIG. 1 shows natural feed 1 being fed into a pyrolysis furnace 2. The hot, cracked, gaseous product 3 of furnace 2 is passed to quench zone 4 for cooling and separation therefrom of liquid pyrolysis gasoline 5. The cooled gaseous product 6 is then passed to compression zone 7 for the liquefaction of C5 and heavier hydrocarbons. Depending on the number of stages of compression employed, some liquid C4's and water can be recovered from this zone. The compressed product 8 is passed to refrigeration zone (cold box) 9 wherein product 8 is cryogenically cooled to less than −240° F. to liquefy essentially all the hydrocarbons left in the product except some methane thereby leaving the relatively pure molecular hydrogen as the predominant gas present. High purity hydrogen is removed from cold box 9 at 10. The liquefied hydrocarbons 11 are passed to demethanation zone 12 from which is separated a methane product 13. The remaining hydrocarbons 15 are passed to a plurality of fractionation zones collectively denoted as 16 from which is recovered a variety of individual products of the plant. Such individual products include, for example, a mixture of ethane and ethylene 17, propylene 18, and a mixture of C4's 19.

In starting up the plant of FIG. 1 pursuant to prior art procedures, furnace 2 was started up using natural feed 1 such as naphtha or gas oil obtained from naturally occurring crude oil. The product of furnace 2 was fed to quench zone 4 and then to compressions zone 7 just as would be done when the plant was at normal operating conditions. Cold box 9 and demethanation zone 12 were then started using the output of zone 7 even though zones 9 and 12 were far warmer than their normal operating temperature. This generated a large amount of gaseous material in zones 9 and 12 that would not normally be present in those zones. These gaseous materials were then removed as streams 10 and 13, and flared or otherwise burned in the atmosphere until units 9 and 12 got down to their normal operating conditions, particularly operating temperatures.

Figure 2:
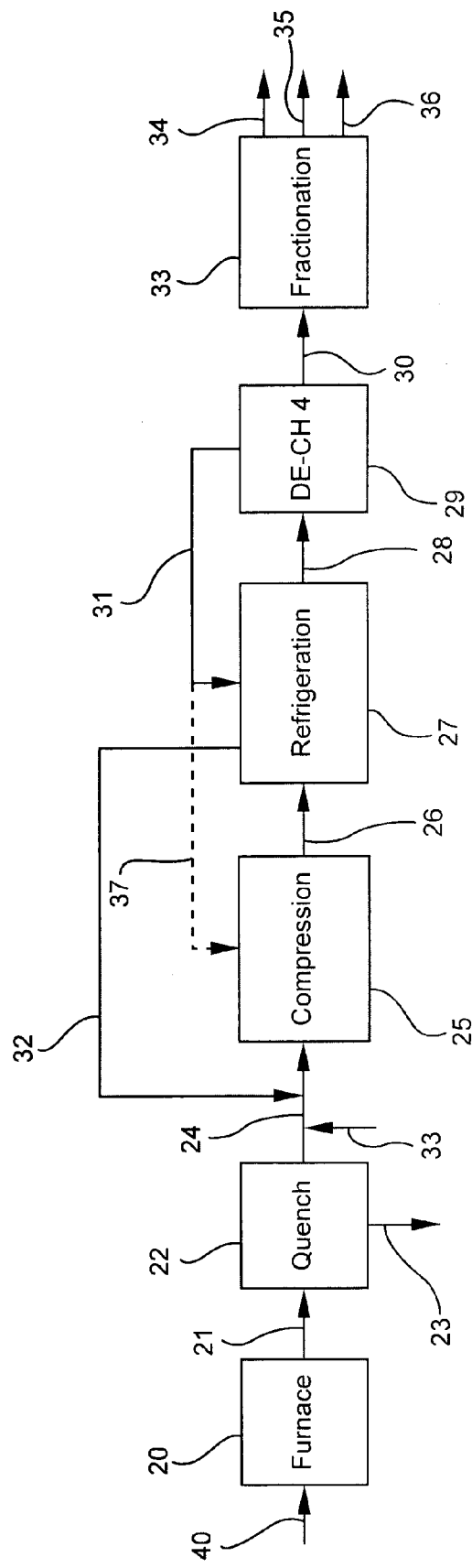
FIG. 2 shows a block flow diagram of the same plant when being started up pursuant to this invention.

In accordance with this invention, as shown in FIG. 2, pyrolysis furnace 20 is operatively connected by stream 21 to quench zone 22 which in turn is connected by stream 24 to compression zone 25. The product of zone 25 is fed to refrigeration zone 27 by stream 26 which in turn feeds demethanation zone 29 by way of stream 28. The product of zone 29 is fed by way of stream 30 to the collective fractionation zone 33.

In the flare-less start up method of this invention, furnace 20 and quench zone 22 are maintained in a non-operating, shut down mode, while zone 33 is maintained in an operating mode. For example, distillation towers in zone 33 are inventoried (filled) and placed on total reflux.

An artificially composed feed is then introduced into the input side of compression zone 25 by way of lines 33 and 24, and compression of the artificial feed 33 begun and continued until zone 25 reaches a pressure of at least about 50% of its normal operational pressure. At this level of pressurization, cooling in cold box 27 is begun while artificial feed to zone 25 is continued. Essentially all gases present and formed in zones 27 and 29 are recycled within the system. Gases from zone 27 are recycled by way of line 32 to the input of zone 25. Gases from zone 29 are initially recycled to zone 27 by way of line 31, and, after zone 27 is close to its operational conditions, recycled to zone 25 as shown by dotted line 37. Essentially none of these recycled gases are vented to the atmosphere with or without flaring of same.

Operation of compression zone 25 and cold box 27 is continued using artificial feed 33 and recycling as aforesaid until these zones reach essentially their normal operating conditions of temperature, pressure, and feed throughput. While this is going on, condensed liquid formed in cold box 27 is removed therefrom and passed by way of line 29 to the demethanation step 31, at which time zone 31 is started up with consequent recycling of gases from zone 31 as aforesaid.

After zones 25, 27, and 29 are approaching or have essentially reached normal operational conditions, furnace 20 is started up using natural feed 40, and, following that, quench zone 22 is started up using cracked natural feed 21 from zone 20. When quench zone 22 is approaching or has essentially reached its normal operating conditions using natural feed, and quenched, cracked natural feed is flowing in line 24 to zone 25, the introduction of artificial feed 33 is terminated. At this point the plant has been started up and returned to its normal operating conditions essentially without flaring or other venting of any gases generated or present during start up.

Since fractionation zone 33 is already in stand-by operation, product from zone 29 can be passed to zone 33 by way of line 30 when this product is suitable for producing therefrom the desired products 34, 35, and 36 which could be ethylene/ethane, propylene, and mixed C4's, respectively.

It should be noted that the system shown in FIG. 2 cannot be started up using natural feed 40 at the outset and simply recycling gases as shown by streams 31, 32, and 37. This is so because when cold box 27 is not cooled to its normal operating conditions insufficient liquid product 28 is formed with the consequence that much larger than normal amounts of gases are formed in cold box 27. If all these gases were recycled to compression zone 25 while feeding natural feed to the furnace, the system would be over pressured. This is so because furnace 20 can physically operate only with a minimum feed, and that minimum feed rate generates a quenched product 24 flow rate to zone 25 that is too large in volume and weight for zone 25 to handle in addition to recycle gases 31, 32, and 37.

Natural feed 40 and quenched gaseous product 24, when obtained from feed 40, can contain at least one of naphthenic, paraffinic, and aromatic hydrocarbons having from 1 to 35, inclusive, carbon atoms per molecule.

Artificial feed 33 is made up of individual components to produce a compositional mixture that is quite different from natural feed 40, but still approximates the hydrocarbonaceous composition of a natural feed to the extent that feed 33 at least minimizes, if not prevents, unnatural (abnormal) condensation of gaseous components to a liquid state in compression zone 25, cold box 27, and demethanation zone 29 during start up. That is to say the artificial feed of this invention has a composition that is chemically substantially less complex than the normal product of zone 22 when operating on a natural feed, and at least minimizes the formation of liquids in zones 25, 27, and 29 that are not otherwise formed in the normal processing of natural feeds. This avoids conditions on start up that can create blockages in the system.

Artificial feed 33 can, for example, consist essentially of two or more of molecular hydrogen, methane, ethane, and propane in essentially the same relative proportions as those compounds are present in the quenched gaseous product 24 when produced from natural feed 40. Preferably, at least two hydrocarbons are present in feed 33. The individual hydrocarbon components in artificial feed 33 can be present in an amount that is within about plus or minus 10 weight percent (wt. %), based on the total weight of artificial feed 33, of the amount of each component in stream 24 when stream 24 is obtained from natural feed 40.

EXAMPLE

In a system substantially as shown in FIG. 2, furnace 20 and quench zone 22 are totally shut down and sitting at ambient temperature and pressure. A natural feed 40 is desired to be used in the system once it is started up and running at normal operating conditions.

The normal feed to the plant during normal operation is comprised of high purity ethane, propane, butane, and heavier liquid feeds such as naphtha and gas oil. Each of these feeds is fed to individual furnaces. Quench product 24 when furnace 20 and quench zone 22 are operating with natural feed 40 has a composition of about 2 to 4 wt. % hydrogen, about 15 to 20 wt. % methane, about 30 to 40 wt. % ethylene, about 10 to 15 wt. % ethane, about 10 to 15 wt. % propylene, and about 7 to 12 wt. % propane, with the remainder being C4 and heavier hydrocarbons, all wt. % based on the total weight of product 24.

The distillation columns in collective fractionation zone 33 each contain fluids that they would normally contain in normal operation, and are maintained at their normal operating conditions at total reflux for each distillation tower.

Zones 25, 27, and 29 are totally shut down and sitting at ambient temperature and pressure.

An artificial feed 33 is formed from individual streams of methane, ethane, and propane to have a composition of about 25 to 30 wt. % ethane, and about 15 to 20 wt. % propane, all wt. % based on the total weight of feed 33.

Artificial feed 33 is introduced into zone 25 and compression start-up begun. The normal operating pressure for zone 25 is about 550 psig. When the pressure in zone 25 reaches about one-half its normal operating pressure, refrigeration zone 27 is started up. Gases recovered from zone 27 during this procedure are recycled in their entirety to the inlet of zone 25. No flaring of these gases is carried out. This is continued until zones 25 and 27 reach their normal operating conditions of temperature, pressure and flow through. While zones 25 and 27 are progressing toward their normal operating conditions using artificial feed 33, condensed liquid formed in zone 27 is passed to zone 29 and start up of that zone commenced.

After zones 25, 27, and 29 have reached essentially their normal operating conditions of temperature, pressure, and flow through, furnace 20 and quench zone 22 are sequentially started up using natural feed 40 as the feed to furnace 20. Until zones 20 and 22 reach their normal operating conditions of temperature, pressure, and flow through, input of artificial feed 33 into zone 25 is continued. When the quenched gaseous product of zone 22 approaches normal operating conditions of temperature, pressure, and flow through, the input of artificial feed 33 to zone 25 is terminated at which time the system as a whole is operating at normal conditions using natural feed 40, but without having vented or flared any gases encountered or formed during the start up procedure.

I claim:

1. In an olefin cracking process wherein a natural hydrocarbonaceous feed is employed in a furnace zone to cause thermal cracking of said natural feed to form a gaseous cracked feed product that contains molecular hydrogen, methane, and other hydrocarbonaceous compounds, said gaseous cracked feed product is passed to a quench zone to cool same and separate a liquid fraction from a quenched gaseous product, said quenched gaseous product is passed to a compression zone to be compressed, the thus compressed quenched gaseous product is cooled in a refrigeration zone to condense to a liquid state components of said natural feed that are desired to be recovered as a product of said cracking process thereby producing a mixture of said liquefied components and non-condensed gases including molecular hydrogen and methane, said mixture being passed to a demethanation zone for removal of said non-condensed gases, said liquefied components being subsequently processed in a fractionation zone to separately remove said liquefied components as final products of said cracking process, and wherein said cracking process is not in a normal operational mode as to temperature, pressure, and natural feed throughput and is in need of start up to achieve said normal operational mode, the improvement comprising 1) maintaining said furnace and quench zones in said non-operational mode, 2) maintaining said fractionation zone in an operating mode as to temperature and pressure and on total reflux, 3) introducing artificial feed gas into said compression zone for subsequent flow into said refrigeration and demethanation zones, said artificial feed having a chemical composition different from said natural feed and being of a composition that approximates the composition of said natural feed to an extent that minimizes condensation of gaseous components to a liquid state in said compression, refrigeration, and demethanation zones when compared to the condensation that would normally occur with said natural feed in said normal operational mode of said cracking process, 4) starting compression of said artificial feed in said compression zone while continuing the introduction of artificial feed until said compression zone is at a pressure of at least about 50% of its normal operational pressure, 5) after reaching at least about 50% of said normal operational pressure in said compression zone starting cooling in said refrigeration zone while continuing the introduction of artificial feed to said compression zone, 6) recycling essentially all gases from said refrigeration zone to the input of said compression zone with essentially no venting of same, 7) continuing said compression and refrigeration zone start up with said gas recycling to said compression zone until said zones reach essentially their normal operating conditions, 8) while said compression and refrigeration zones are progressing toward their normal operating conditions, removing condensed liquid formed in said refrigeration zone from that zone and passing said liquid to said demethanation zone, and starting operation of said demethanation zone, 9) after said compression, refrigeration, and demethanation zones have started up, starting up said furnace and quench zones while introducing natural feed into said furnace zone, and 10) when said quenched gaseous product from said quench zone approaches normal operating conditions while employing natural feed, terminating said introduction of artificial feed.

2. The method of claim 1 including removing gaseous components from said demethanation zone during start up of same and returning same to at least one of said compression zone and said refrigeration zone, and when said demethanation zone reaches normal operating conditions passing liquid there from to said fractionation zone.

3. The method of claim 1 wherein said natural feed and said quenched gaseous product obtained from said natural feed contains at least naphthenic, paraffinic, and aromatic hydrocarbons having from 1 to 35, inclusive, carbon atoms per molecule, and said artificial feed contains at least two of molecular hydrogen, methane, ethane, and propane in approximately the same proportions as those compounds are present in said quenched gaseous product when produced from said natural feed.

4. The method of claim 3 wherein said quenched gaseous product from said natural feed contains at least two of molecular hydrogen, methane, ethane, and propane, and said artificial feed contains at least the same components in approximately the same proportions as they are present in said quenched gaseous product obtained from said natural feed.

5. The method of claim 3 wherein said proportion of each of said components present in said artificial feed is within about 10 wt. % of the amount of each of those components in said quenched gaseous product obtained from said natural feed.

\* \* \* \* \*